(12) United States Patent
Wachowicz et al.

(10) Patent No.: US 10,775,460 B2
(45) Date of Patent: Sep. 15, 2020

(54) IMAGE GUIDED RADIATION THERAPY SYSTEM

(71) Applicant: Alberta Health Services, Edmonton (CA)

(72) Inventors: Keith Wachowicz, Edmonton (CA); B. Gino Fallone, Edmonton (CA); Brad Murray, Sherwood Park (CA)

(73) Assignee: ALBERTA HEALTH SERVICES, Edmonton, AB (CA)

( * ) Notice: Subject to any disclaimer, the term of this patent is extended or adjusted under 35 U.S.C. 154(b) by 296 days.

(21) Appl. No.: 15/636,188

(22) Filed: Jun. 28, 2017

(65) Prior Publication Data

US 2019/0004131 A1   Jan. 3, 2019

(51) Int. Cl.
| | | |
|---|---|---|
| *A61B 5/05* | (2006.01) | |
| *G01R 33/48* | (2006.01) | |
| *A61N 5/10* | (2006.01) | |
| *G01R 33/38* | (2006.01) | |
| *A61B 5/055* | (2006.01) | |

(52) U.S. Cl.
CPC ....... *G01R 33/4808* (2013.01); *A61N 5/1049* (2013.01); *A61N 5/1077* (2013.01); *A61B 5/055* (2013.01); *A61N 2005/1055* (2013.01); *G01R 33/3806* (2013.01); *G01R 33/4812* (2013.01)

(58) Field of Classification Search
None
See application file for complete search history.

(56) References Cited

U.S. PATENT DOCUMENTS

| | | | |
|---|---|---|---|
| 8,958,528 B2 | 2/2015 | Fallone et al. | |
| 8,983,573 B2 | 3/2015 | Carlone et al. | |
| 2007/0052420 A1* | 3/2007 | Speck | G01R 33/3875 324/320 |
| 2014/0184372 A1* | 7/2014 | Mathieu | G01R 33/3856 336/60 |
| 2015/0217136 A1* | 8/2015 | Stanescu | A61N 5/1049 600/411 |

OTHER PUBLICATIONS

Poole, M. et al., *Novel Gradient Coils Designed Using a Boundary Element Method*, Concepts in Magnetic Resonance Part B: Magnetic Resonance Engineering (Aug. 2007) 1:31(3):162-175.

* cited by examiner

*Primary Examiner* — Joel F Brutus
(74) *Attorney, Agent, or Firm* — Alston & Bird LLP

(57) ABSTRACT

A magnetic resonance (MR)-radiotherapy (RT) hybrid system for treating a patient is disclosed. The MR-RT hybrid system includes a radiation source for supplying a radiation beam to treat the patient and an MR imaging (MRI) apparatus for generating a divergent gradient field shaped to match a divergent geometry of the radiation beam of the radiation source.

16 Claims, 12 Drawing Sheets

IMAGE GUIDED RADIATION THERAPY SYSTEM

The present invention relates generally to magnetic resonance guided radiotherapy treatment systems and, specifically, to an apparatus and method for magnetic resonance guided radiotherapy treatment with beam's eye view imaging.

BACKGROUND

Image guided radiotherapy (IGRT) has become the state of the art in radiation treatment. IGRT may utilize two-dimensional (2D) projection images or three-dimensional (3D) cone beam computed tomography (CT) images that are acquired prior to treatment. These images are compared to a set of pre-treatment images to ensure the patient has been set up accurately and consistently each treatment session. While CT, for example reconstructs in a standard cartesian geometry, the geometry of the radiation treatment beam originates from a divergent source. Beam's eye view (BEV) projection is commonly used to visualize patient anatomy to determine exactly what tissue will be irradiated from the divergent treatment beam.

In BEV projection, the 3D image dataset captured by CT, referred to as the portal image, is registered to a reconstructed BEV image. The BEV image is reconstructed by ray tracing through the 3D CT dataset of the portal image from a virtual source position aligned with the location of the target of the radiation treatment beam source. Since the BEV image represents the path of the divergent radiation treatment beam, target coverage and critical structure avoidance can be accurately determined. This makes the BEV image an ideal image to use for real-time IGRT where the image must be acquired and analyzed in real time to reposition the beam to conform to the target volume while avoiding any surrounding radiation sensitive organs. However, processing the CT dataset in real time to generate a BEV image is computationally intensive and cannot be completed in real-time.

Magnetic resonance (MR) guided radiotherapy treatment systems integrate magnetic resonance imaging (MRI) devices with radiotherapy treatment systems. For example, U.S. Pat. No. 8,983,573, incorporated by reference in its entirety herein, is directed to a radiation therapy system that comprises a combined MRI apparatus and a linear accelerator capable of generating a beam of radiation.

In MRI, a signal from a slab of selected tissue gives rises to a two-dimensional slice that is integrated in a direction perpendicular to the slab. If the slab is oriented horizontally, each pixel in the 2D image is generated by summing the signal together along a vertical line. A radiation beam originating from a radiation source (a point source location) diverges from the source and fans out over the target. Thus, targeting the radiation source based on this conventionally obtained image may lead to a decreased radiation dose at the target than what was planned and/or unnecessary dose to tissue surrounding the target. For example, a 5 cm thick image slice may result in up to 4 mm of targeting error, 15 cm from the central beam axis, assuming a 100 cm distance from the radiation source. This effect will increase further as slice thickness increases.

While it may be possible to process the image data collected in MRI by ray tracing to produce an BEV image, similar to the methodology described above for CT, this processing is performed after the data is captured and therefore not available in real-time. Furthermore, the 3D image data collected in MRI requires significantly more data acquisition in general than does the image data collected in CT. As a result, significant time is required to produce a BEV image.

Accordingly, it is an object of the present invention to obviate or mitigate at least one of the above-noted disadvantages.

BRIEF SUMMARY

In accordance with an aspect of an embodiment, there is provided a magnetic resonance (MR)-radiotherapy (RT) hybrid system comprising: a radiation source configured to supply a radiation beam to treat the patient; and an MR imaging (MRI) apparatus configured to generate a divergent gradient field shaped to match a divergent geometry of the radiation beam of the radiation source.

BRIEF DESCRIPTION OF THE SEVERAL VIEWS OF THE DRAWING(S)

Embodiments of the invention will now be described by way of example only with reference to the following drawings in which.

DETAILED DESCRIPTION OF THE EMBODIMENTS

Figure 1:
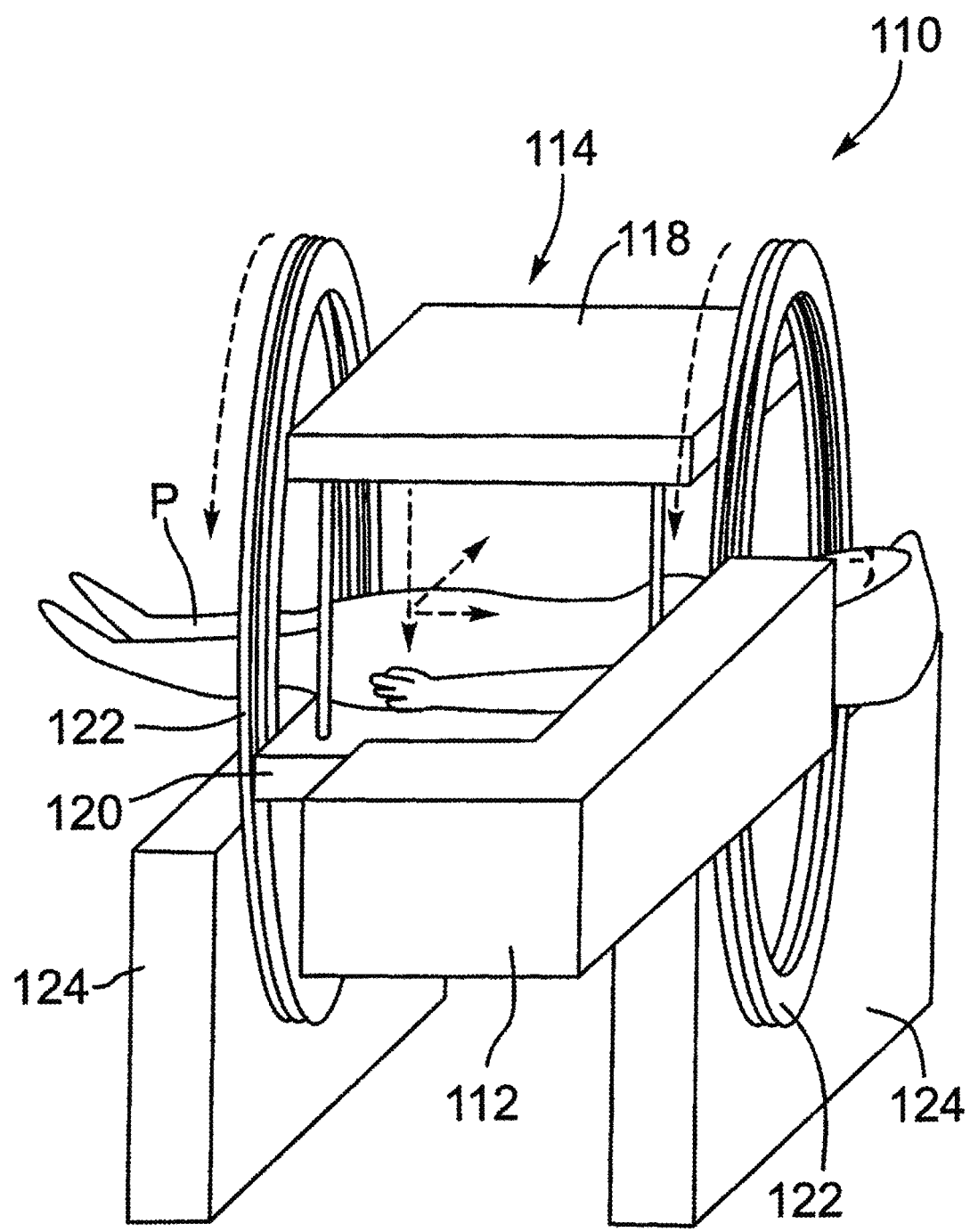
FIG. 1 is an isometric view of an integrated radiation source and magnetic resonance imaging (MRI) system.
Figure 2:
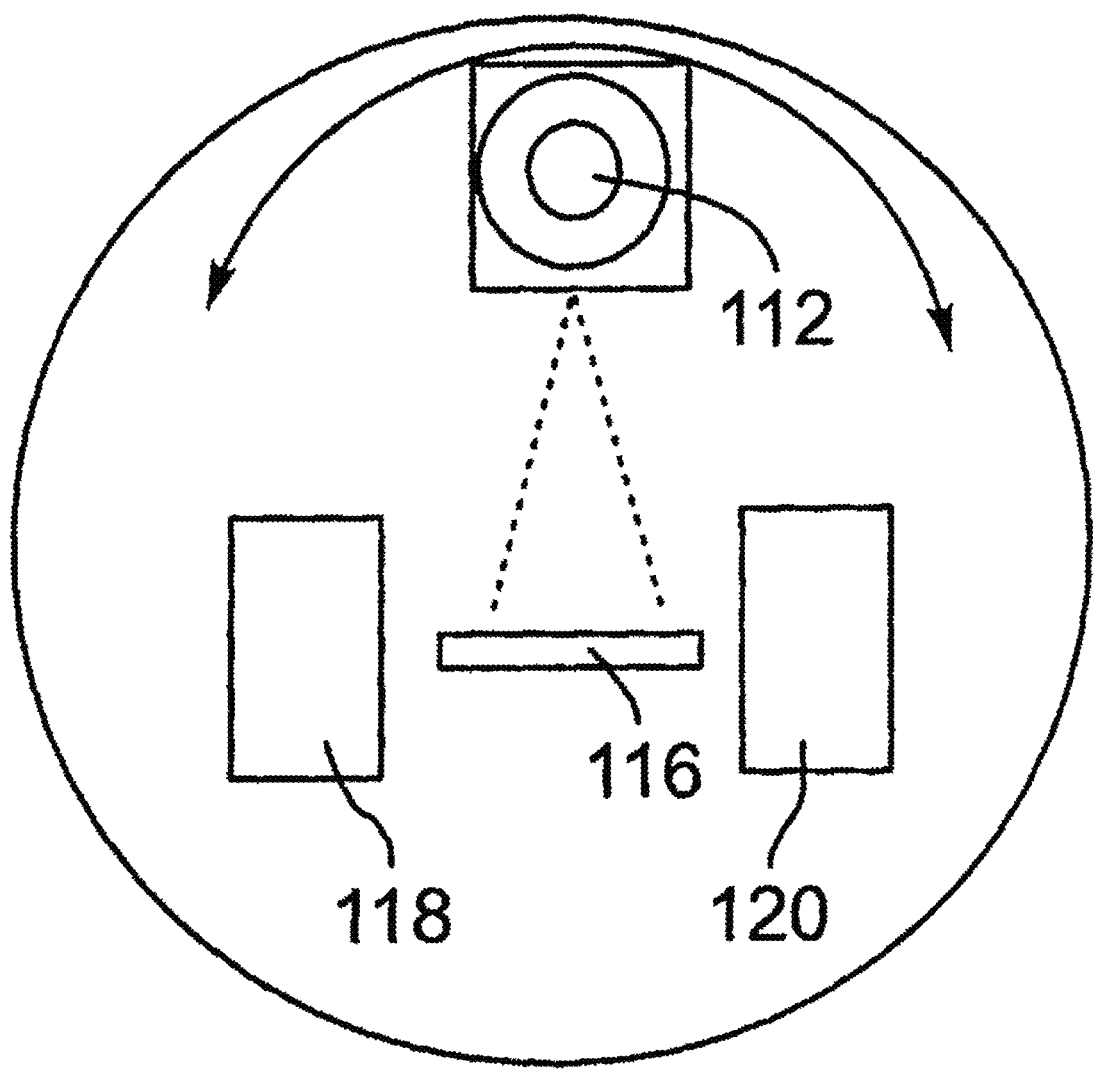
FIG. 2 is a view in a transverse plane of the integrated linear accelerator and MRI system of FIG. 1.
Figure 3:
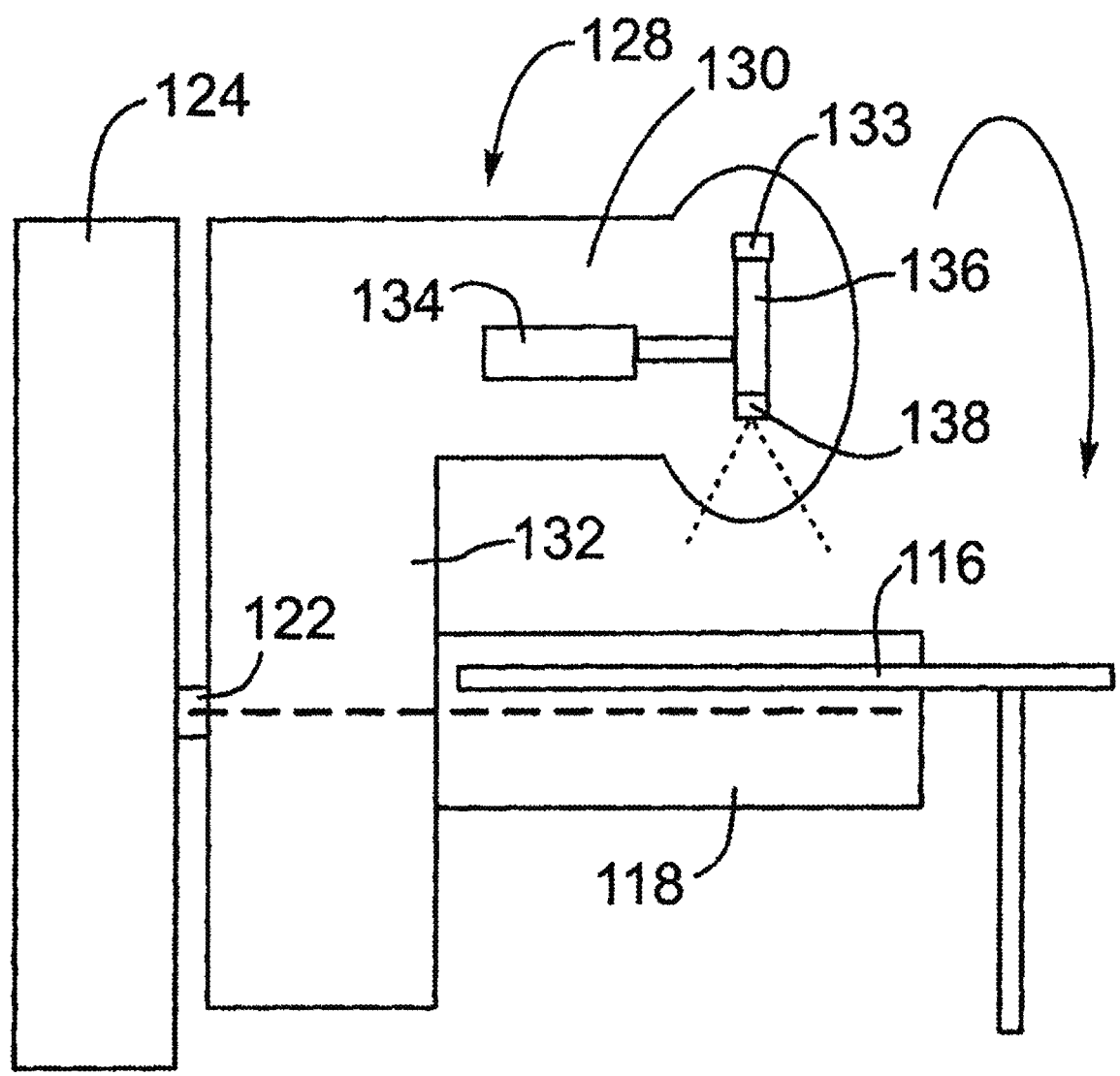
FIG. 3 is a view in a saggital plane of the integrated linear accelerator and MRI system of FIG. 1.

For convenience, like numerals in the description refer to like structures in the drawings. Referring to FIGS. 1 to 3, an integrated radiation source and MRI system is shown and is generally identified by reference numeral 110. As can be seen, the integrated radiation source and MRI system 110 includes a radiation source and an MRI apparatus 114. In this embodiment, the radiation source is a linear accelerator or linac 112. As will be described, the linac 112 is configured to generate a treatment beam. The MRI apparatus 114 is configured to image a patient in real-time. The linac 112 and the MRI apparatus 114 are coupled to a rotatable gantry 122 so that they can be rotated in unison to treat a patient P.

In this particular example, the MRI apparatus 114 comprises a biplanar magnet having a pair of opposing magnet poles 118 and 120 creating a 0.2 T magnetic field strength. The MRI apparatus 114 is an open bore type including a table 116 on which the patient P can lay. In FIG. 1, the magnet poles 118 and 120 of the biplanar magnet are disposed above and below the table 116. The linac 112 and magnet poles 118 and 120 are mounted on the gantry 122 that is supported by a frame 124. In FIG. 2, the gantry 122 is rotated, and the magnet poles 118 and 120 of the biplanar magnet are disposed on the left-hand side and right-hand side of the table 116, respectively.

The linac 112 includes a head 128 housing an electron beam generator 130 mounted on an arm 132 that is affixed to the gantry 122. In this manner, the linac 112 rotates in unison with the gantry 122 and thus, maintains its position relative to the magnet poles 118 and 120. If desired, the linac 112 may have its own gantry. In this case, the gantry of the linac 112 and the gantry 122 are mechanically coupled so that the linac 112 rotates in unison with the magnet poles 118 and 120.

The electron beam generator 130 includes an electron gun 133, an RF generator 134, an accelerating waveguide 136, a heavy metal target 138 at one end of the accelerating waveguide 136 and a beam collimating device (not shown). Interference reducing structure is also provided to inhibit the linac 112 and MRI apparatus 114 from interfering with one another during operation.

Alternatively, the linac 112 and MRI apparatus 114 may be mechanically coupled so that the electron beam is directed horizontally, and the magnet poles 118 and 120 are mounted vertically such that the magnetic field is horizontal, but perpendicular to the electron beam. These two components are fixed and non-movable. Variable angle electron or photon beam delivery is allowed by rotating the subject while in a sitting position. This integrated linac and MRI system configuration is particularly useful for lung cancer subjects who prefer standing/seating to laying supine, and for whom, conventional CT simulation does not allow simulation in the sitting position.

Further specifics of the integrated radiation source and MRI system 110 are described in Applicants' U.S. Pat. Nos. 8,958,528 and 8,983,573, the contents of which are incorporated by reference. Additionally, other systems designed to integrate a linac with an MRI system may also be employed.

The MRI apparatus 114 comprises an MRI system that comprises a main magnet, gradient coils, a radio frequency (RF) coil and a scanner. The main magnet is configured to produce a magnetic field that aligns the hydrogen atoms of the patient P placed on the table with the direction of the magnetic field produced by the main magnet. In this embodiment, the main magnet is a biplanar magnet. The gradient coils are configured to produce a magnetic gradient field distribution that is generally weaker than the magnetic field produced by the main magnet. The magnetic gradient field distribution is superimposed on top of the magnetic field produced by the main magnet. The RF coil is configured to apply a RF pulse that is directed toward the area to be scanned. The RF pulse is configured to excite atoms to produce signals, which are then detected by RF receivers. The gradient coils are configured to localize the signal, first by defining the region of excitation affected by the RF pulse, and then by localizing the signal within a slice or slab of the area being scanned to generate images of the slide or slab.

Figure 4:
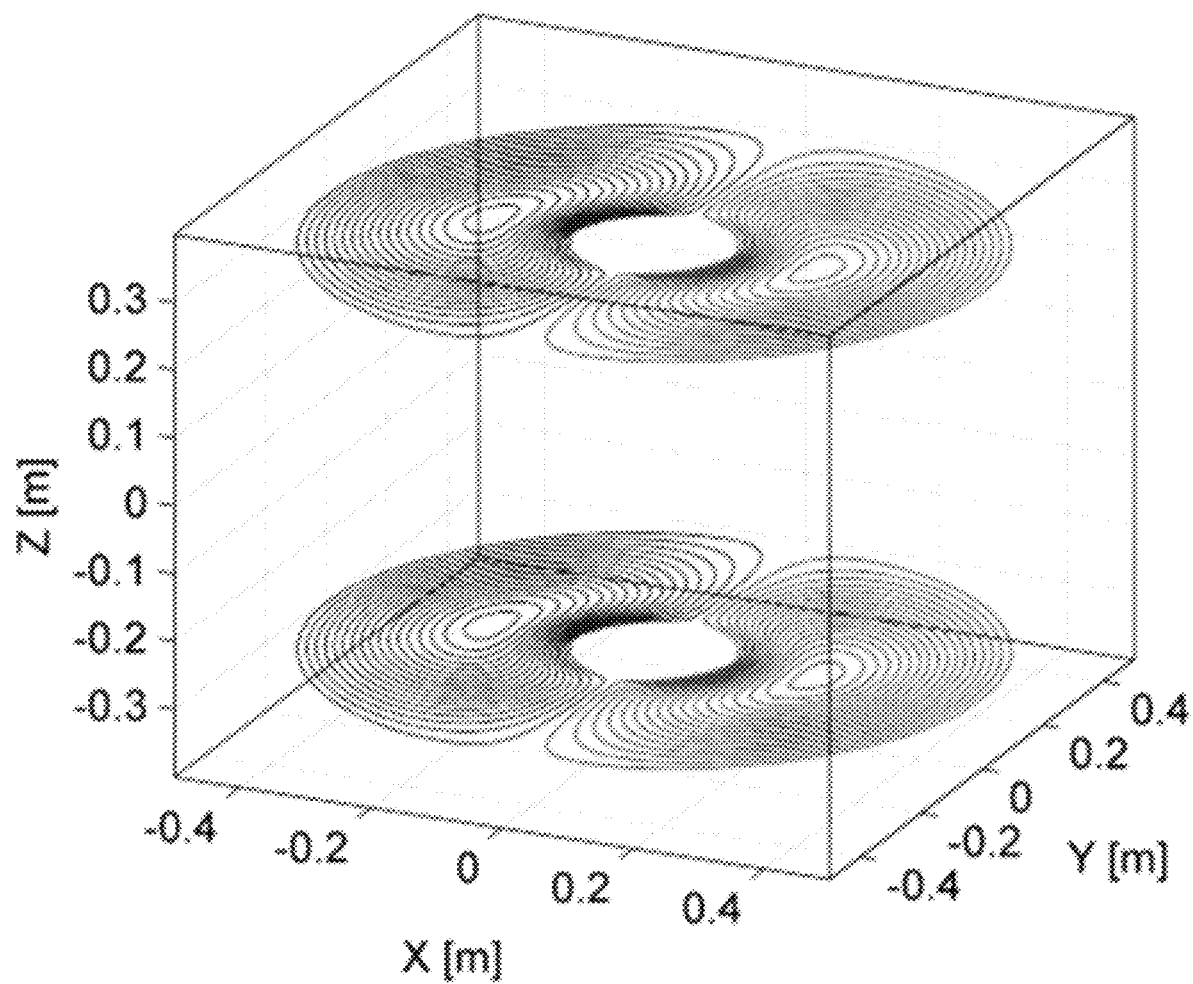
FIG. 4 is plan view of a transverse gradient coil for the MRI system of FIG. 1.

The gradient coils are configured to produce linearly varying magnetic fields for spatial localization of the magnetic signal and image production. An example of winding patterns of gradient coils for the biplanar MRI system 114 is depicted in FIG. 4. In this example, the gradient coil varies the magnetic field in a direction perpendicular to the magnetic field produced by the main magnetic. The windings on the right and left sides of FIG. 4 depict current loops that circulate in different directions (clockwise versus counter-clockwise). Gradient coils having the winding patterns illustrated in FIG. 4 would be positioned with the current paths adjacent to pole plates above and below the patient P in the system 110.

Figure 5:
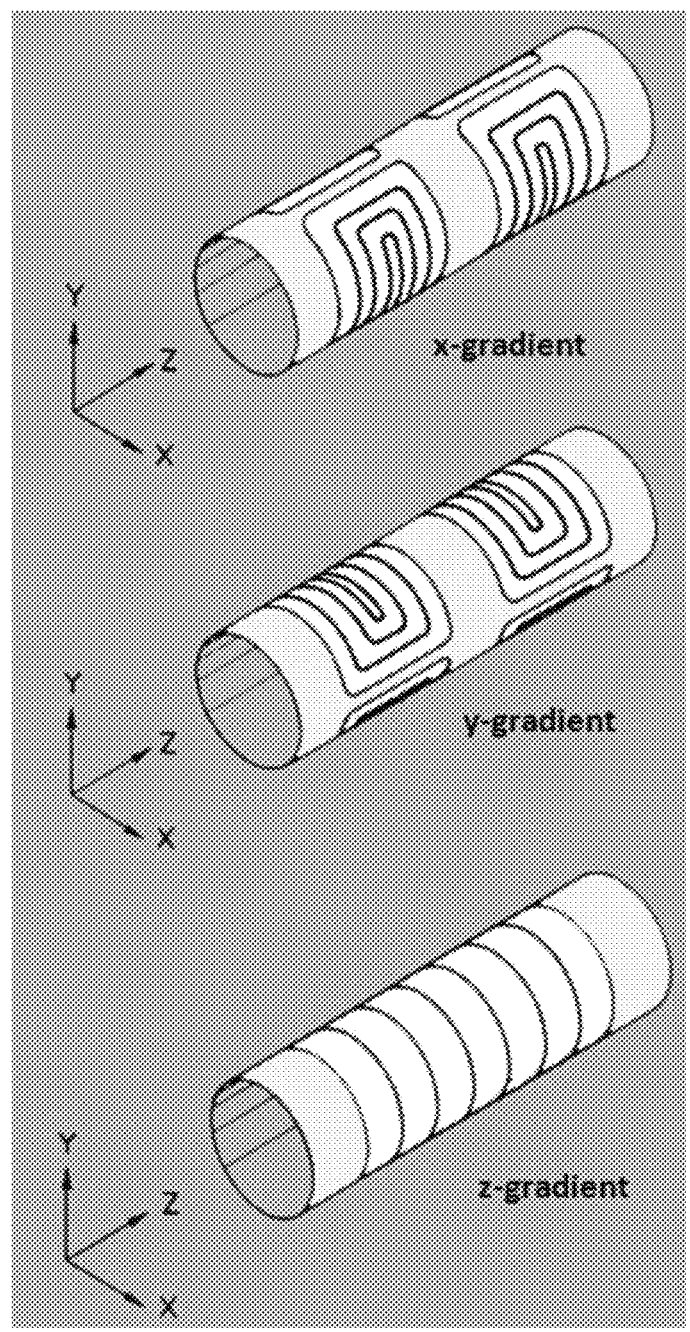
FIG. 5 is an isometric view of another embodiment of a set of gradient coils for an MRI system using a cylindrical magnet.

Although the MRI apparatus is described using biplanar magnets, cylindrical magnets may also be used. Gradient coil winding patterns for cylindrical MRI systems are illustrated in FIG. 5. As illustrated in FIG. 5, three sets of gradient coils may be employed. In such an embodiment, each gradient coil is driven by an independent power amplifier and creates a magnetic gradient field whose z-component varies linearly along the x-, y- and z-directions. The x and y gradient coils are transverse coils. The z gradient coil is a longitudinal gradient coil. The x and y gradient coils have a saddle (Golay) coil configuration. The z gradient coil has a circular (Maxwell) coil configuration.

As previously stated, the linac 112 includes a beam collimating device (not shown). In this embodiment, the beam collimating device is a multileaf collimator (MLC) that is configured to shape the treatment beam radiating from the linac 112.

Figure 6:
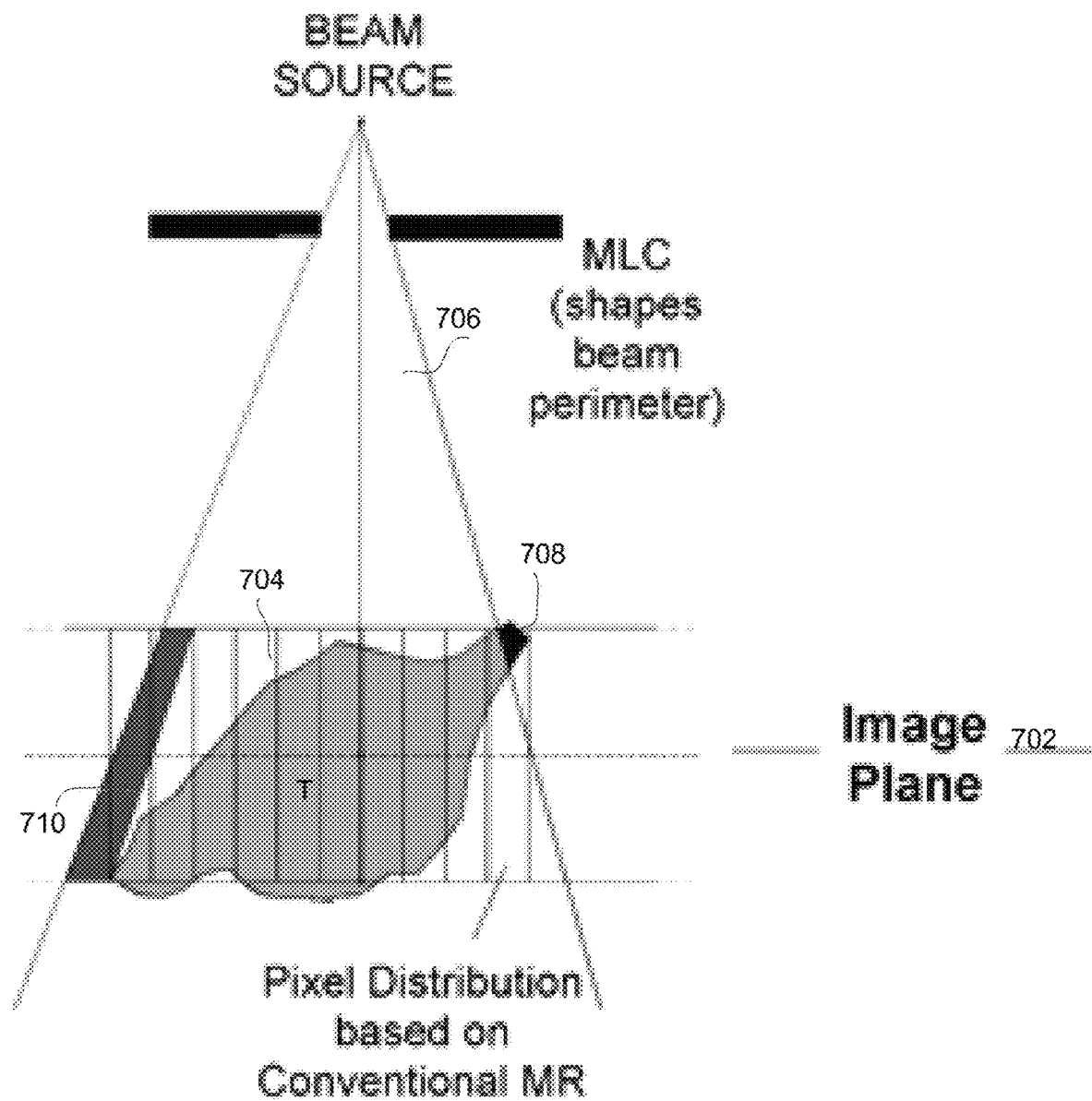
FIG. 6 is a schematic view of a radiation beam used to target patient tissue based on images encoded from a magnetic field produced by a conventional gradient coil configuration.

As described above, in conventional systems, the linac 112 is configured to aim the treatment beam based on MRI imaging using the conventional coordinate systems generated by the gradient coils of the MRI apparatus 114. Referring to FIG. 6, the problem of making targeting decisions for the linac 112 based on MRI images created using conventional coordinate systems is illustrated. In the conventional coordinate system, targeting decisions are made on pixels that summed in a direction perpendicular to an image plane 702. The images slices 704 used by the MRI apparatus to create an MRI image are in a direction perpendicular to a source-to-isocenter axis. However, the treatment beam 706 diverges as it travels from the linac. As a result of this divergence, a part 708 of the target tumor T may not be treated even though it will appear on the MRI image to be within a path of the treatment beam. Similarly, healthy tissue 710 may be unnecessarily radiated by the treatment beam even though it will not appear on the MRI image to be within the path of the treatment beam. As will be appreciated, such divergence results in incomplete treatment of the patient's condition as well as significant radiation of healthy tissue which can have adverse side effects.

Figure 7:
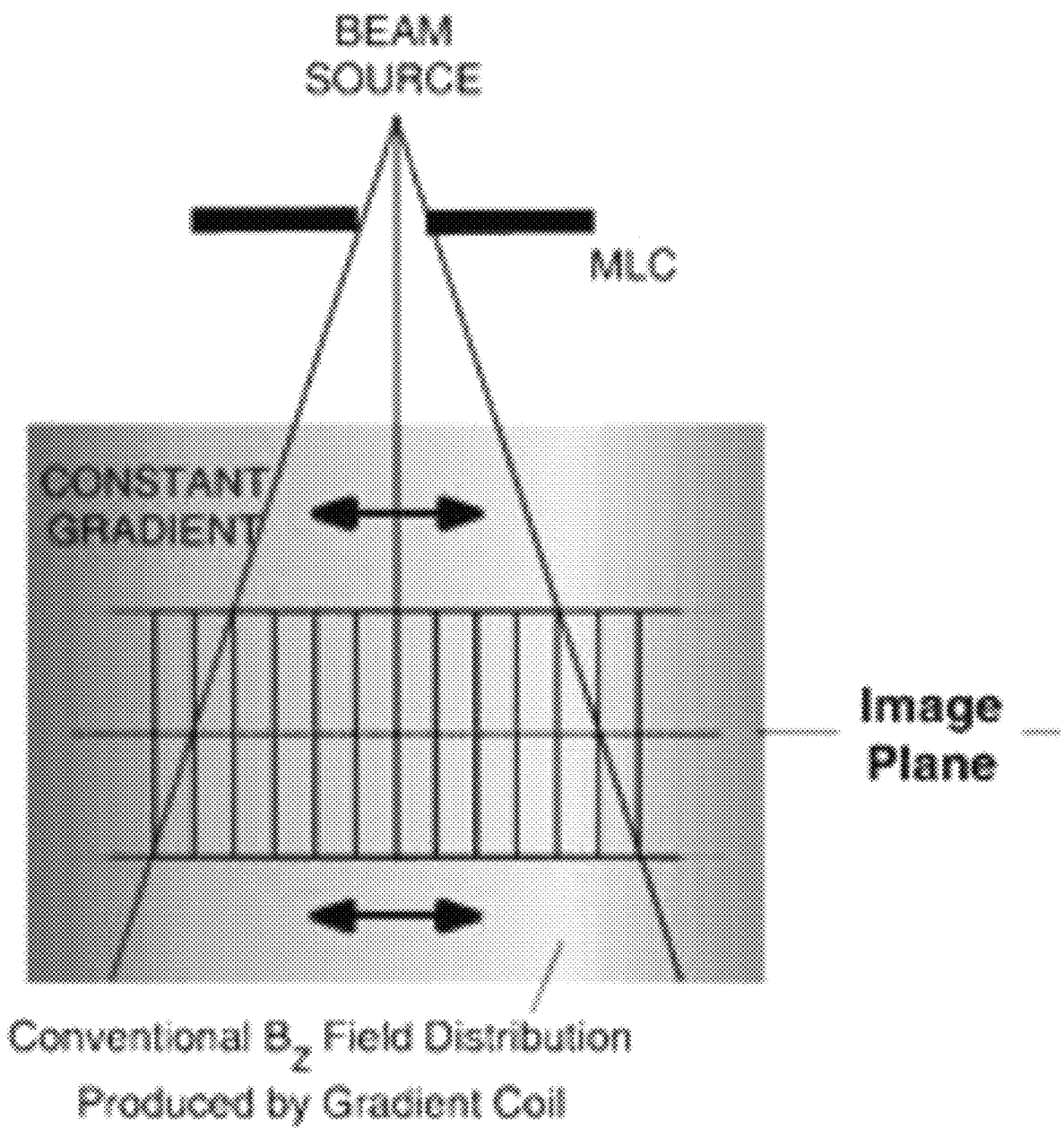
FIG. 7 is a schematic view of the magnetic field produced by a conventional gradient coil configuration.

The in-plane encoding gradient of the MRI apparatus 114 is given by Equation 1.

$$G_i(x,y,z) \propto \hat{r}_i \cdot \langle x,y,z \rangle \qquad \text{Equation 1}$$

Where $\hat{r}_i$ represents a unit vector identifying one of the encoding directions within the plane of the imaging slice. FIG. 7 depicts a qualitative pattern of the encoding field distribution of the magnetic field $B_z$ produced by gradient coils, which are used to allow for spatial encoding within the plane of the imaging slab. As will be appreciated, the field variation is the same at all "vertical" positions within the imaging slab.

In accordance with an embodiment, the gradient coils of the MRI apparatus 114 are configured to generate a divergent magnetic gradient field shaped to match the divergent geometry of the treatment beam emanating from the radiation source. Thus, the radiation beam is considered to be emanating from a point source. As such, the divergent geometry of the treatment beam will depend on the distance of the radiation source from the imaging isocenter. The divergent magnetic gradient field is shaped such that image pixels scanned by the RF detector are summed over the same divergent path as the treatment beam produced by the linac 112. Targeting decisions for the linac 112 are made based on pixels acquired from the gradient coils of the MRI apparatus 114 which images the patient using a divergent perspective as per the divergent magnetic gradient field.

Figure 8:
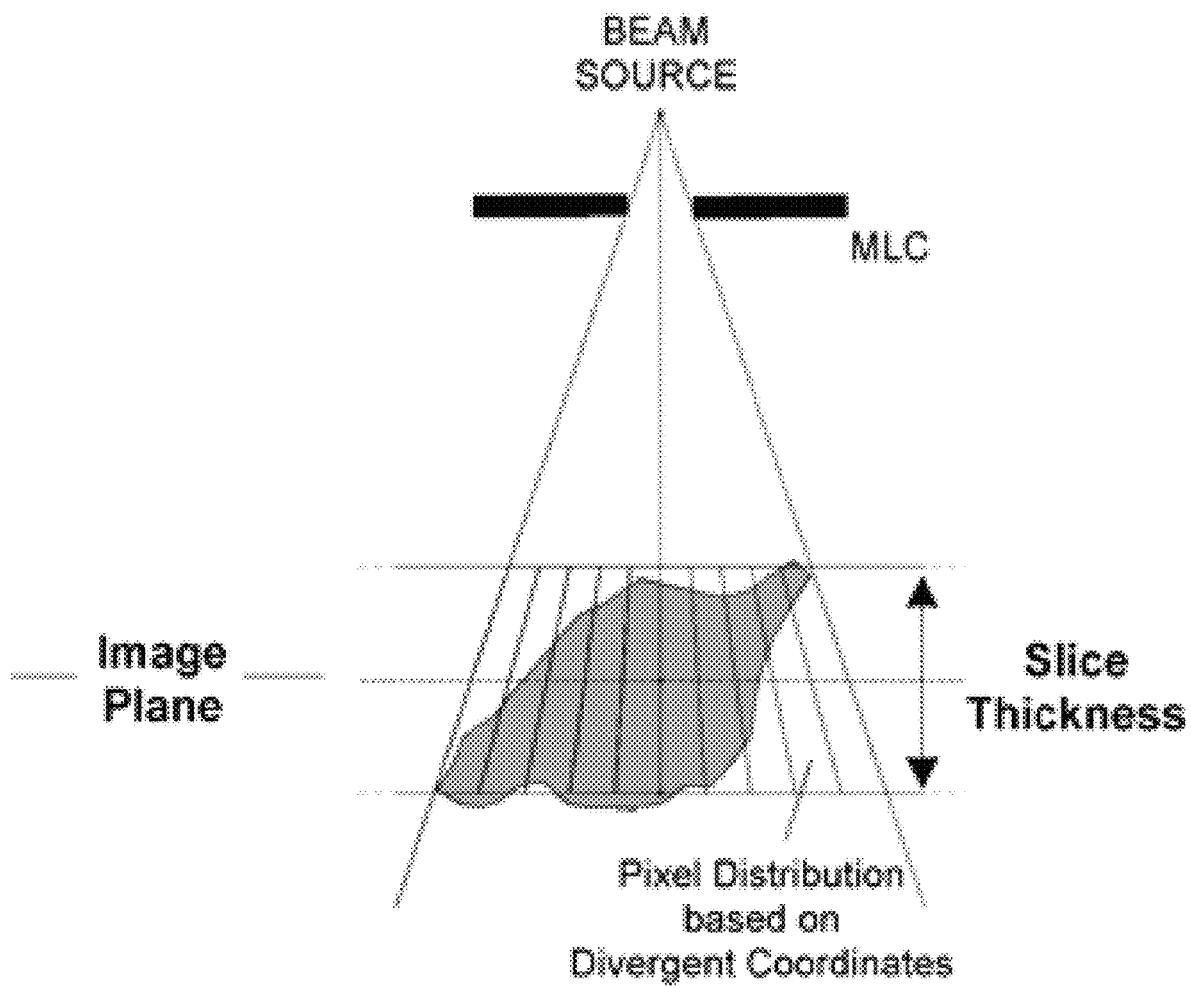
FIG. 8 is a schematic view of the radiation beam used to target patient tissue based on images encoded from a divergent magnetic field produced by a gradient coil configuration in accordance with an embodiment of the invention.

FIG. 8 illustrates benefits of making targeting decisions for the linac 112 based on MRI images created using the divergent coordinate system of the gradient coils of the MRI apparatus 114. In the divergent coordinate system, targeting decisions are made on image pixels that summed in a direction in-line with the divergent direction of the treatment beam of the linac 112. That is, the image slices used by the MRI apparatus 114 to create an MRI image mimic the shape of the treatment beam. As a result, the treatment beam is more likely to radiate all of the targeted tissue of the tumor, while minimizing radiation of healthy tissue adjacent to the tumor. Thus, the using of a divergent gradient magnetic field minimizes adverse side effects and more completely treats the target tumor.

The in-plane encoding gradient of the MRI apparatus 114 is given by Equation 2.

$$G_i(x, y, z) \propto \frac{SID}{SID + \hat{r}_s \cdot \langle x, y, z \rangle} \hat{r}_i \cdot \langle x, y, z \rangle \qquad \text{Equation 2}$$

As previously stated, $\hat{r}_i$ represents a unit vector identifying one of the encoding directions within the plane of the imaging slice. In a BEV image, this will typically be one of the in-plane encoding directions. In equation 2, $\hat{r}_s$ represents a unit vector identifying a direction of the axis connecting the radiation source and imaging isocentre (referred to as the source-to-isocenter axis). In a BEV image, this will typically be the vector perpendicular to the image plane. Furthermore, SID represents the distance between the radiation source and the magnetic isocenter of the MRI apparatus 114.

In this embodiment, the in-plane encoding gradient is altered from the encoding gradient of Equation 1 to equal or approximate the encoding gradient of Equation 2 by altering the winding patterns of the gradient coils of the MRI apparatus 114 to produce a divergent coordinate system.

The gradient coils are configured to generate a divergent magnetic gradient field shaped to match the radiation beam of the radiation source. In one embodiment, the gradient coils are produced and designed in a similar manner to conventional gradient coils, but are designed with altered winding patterns to generate the required divergent gradient field distributions in line with the treatment beam. These winding patterns are typically derived numerically through a variety of established methods and can be optimized to approximate any desired field pattern. For example, Poole M., Bowtell R. Novel gradient coils designed using a boundary element method. Concepts in Magnetic Resonance Part B: Magnetic Resonance Engineering. 2007 Aug. 1; 31(3):162-75, which is incorporated herein by references, describes methods of deriving winding patterns. However, such a configuration would permanently acquire images only in a divergent frame.

If it is desired to provide the system with extra flexibility, additional gradient coils can be added to the conventional gradient coils. In an aggregate configuration, the additional gradient coils are configured to modify the transverse gradient field to the desired divergent magnetic field. Alternatively, in a separate configuration, the additional gradient coils are configured to provide the desired divergent magnetic field on their own. In both the aggregate and separate configurations, the additional gradient coils may be controlled independently from the conventional gradient coils.

Thus, if the additional gradient coils are not activated, MRI imaging is performed using the conventional gradient coils in a standard, transverse Cartesian coordinate system. In the aggregate configuration, if the additional coils are activated, MRI imaging is performed using a combination of the additional coils and the conventional coils to provide the divergent coordinate system. In the separate configuration, if the additional coils are activated, MRI imaging is performed using the additional coils alone in order to provide the divergent coordinate system.

In a system in which the gradient coils and radiation source are configured to rotate in unison, such as the one described above, the minimum number of additional coils to generate a divergent geometry in both in-plane encoding directions is two; one coil for each of the two axes perpendicular to the source-to-isocenter axis. As will be appreciated by one of skill in the art, additional coils could be used.

Figure 9:
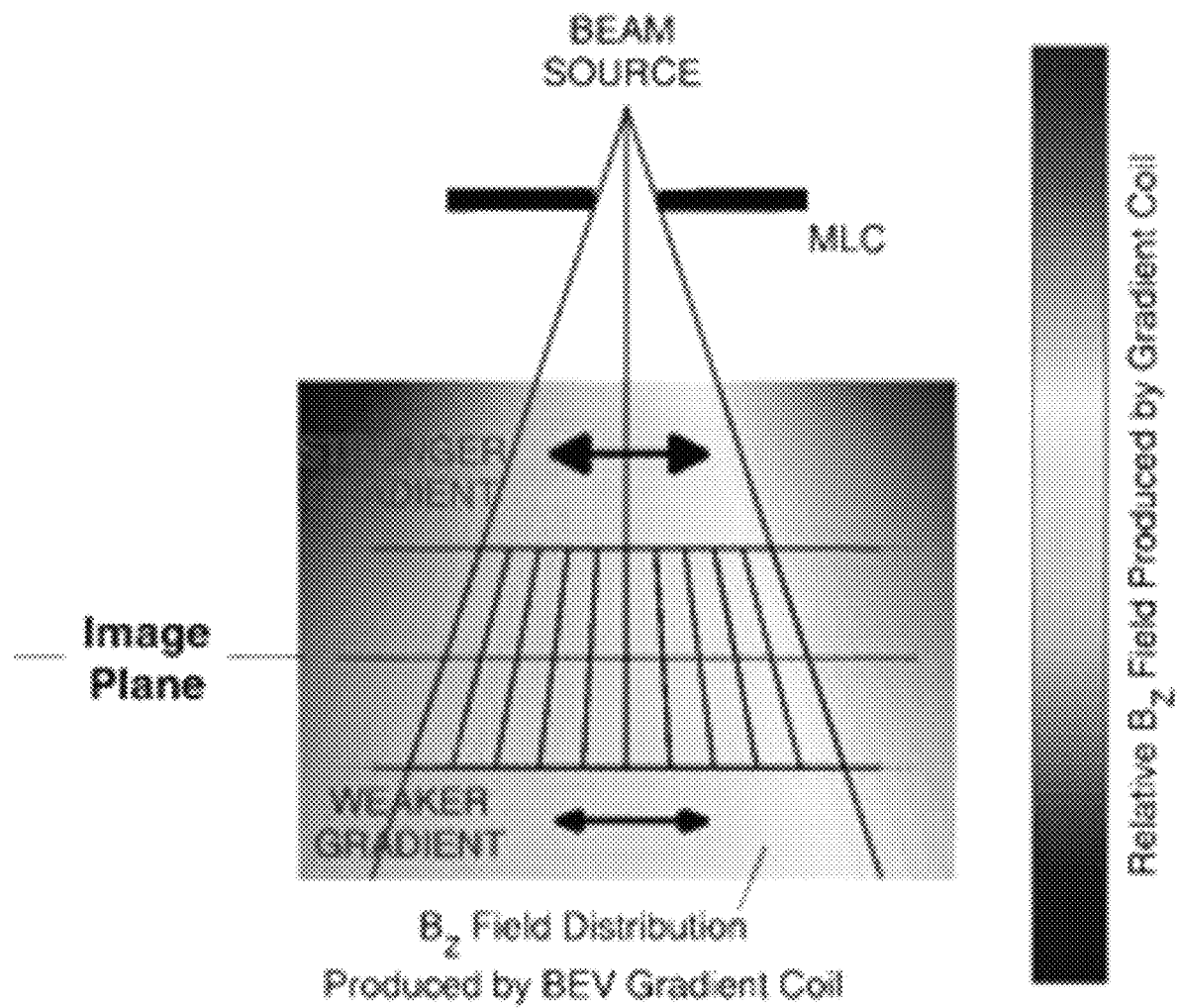
FIG. 9 is a schematic view of the divergent magnetic field produced by the gradient coil configuration in accordance with an embodiment of the invention.

A qualitative pattern of the encoding field distribution $B_z$ of the gradient coils of the MRI apparatus 114 is displayed in FIG. 9. The magnetic field $B_z$ produced by gradient coils of the MRI apparatus 114 is used to allow for spatial encoding within the plane of the imaging slab. The in-plane encoding gradient is configured for Beam's Eye View (aligned with the linac 112 treatment geometry) imaging. The field pattern has a stronger variation at some "vertical" positions within the slab than at others, allowing the imaging to inherently represent a divergent geometry.

In the embodiments described above, the gradient coils and the linac are fixed to a gantry so that they rotate in unison. However, a system in which the gradient coils do not rotate with the radiation source will also benefit from the generating a divergent gradient coordinate system described above. However, it may not be possible to design gradient coils that generate divergent magnetic gradient fields shaped to match all possible positions of the treatment beam, as the direction of the treatment beam is constantly changing with the rotation of the radiation source. However, the desired magnetic gradient fields can be effectively approximated by an optimized combination of a set of additional coils that generate non-linear magnetic field distributions in addition to the conventional gradient coils.

The additional set of coils can be the "$2^{nd}$ order" field gradients that are often used for shimming. These coils consist of a winding pattern that produces $B_z$ field patterns that correspond to the second-order spherical harmonic functions. While many magnets already have such sets of coils, they are typically not engineered to handle the power requirements of imaging, and would have to be specifically designed for this function by generating winding pathways with different criteria such as lower overall resistance and inductance.

There are five of spherical harmonic functions, and a coil is required to produce each of them. If a divergent geometry is required for any arbitrary image orientation in the magnet geometry, five coils may be necessary to approximate the field relationship in Equation 2 in conjunction with the conventional gradient coils. However, only four coils would be required if it can be assumed that the BEV image plane will always be parallel to the axis of gantry rotation. This assumption regarding the orientation of the BEV image plane would allow one of the five harmonic fields to be omitted. Thus, only four coils are required.

Figure 10:
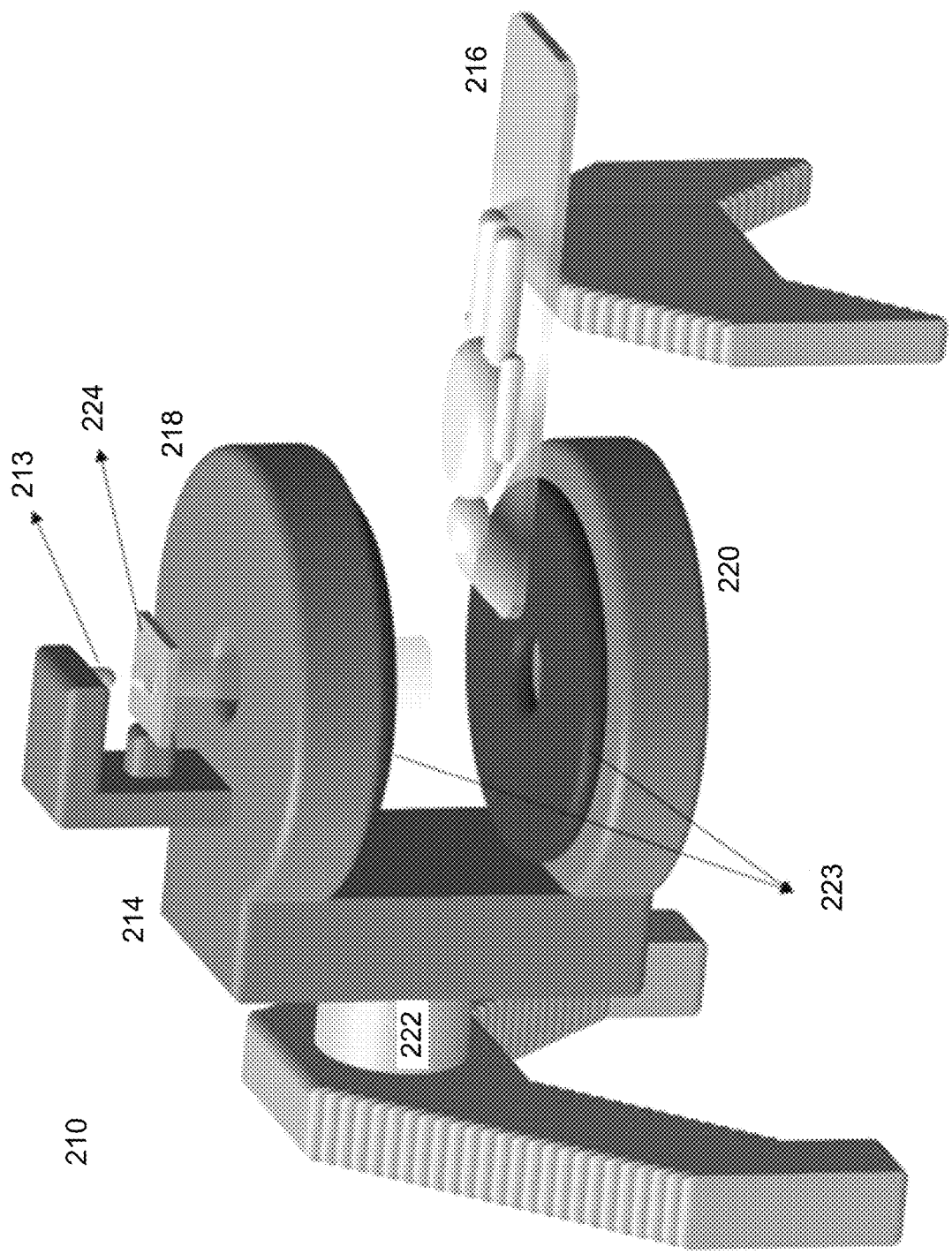
FIG. 10 is an isometric view of another embodiment of an integrated radiation source accelerator and magnetic resonance imaging (MRI) system.

While a particular integrated radiation source and MRI system has been described, one of skill in the art will appreciate that other configurations are possible. Turning now to FIG. 10, another embodiment of an integrated radiation source and MRI system is shown and is generally identified by reference numeral 210. As can be seen, the integrated radiation source and MRI system 210 comprises a radiotherapy radiation source 213, a biplanar MRI magnet assembly 214, a patient treatment couch 216 and a rotating gantry 222. The radiotherapy radiation source 213 is configured to generate a treatment beam. The MRI magnet assembly 214 is configured to image a patient positioned on the patient treatment couch 216 in real time. The radiotherapy radiation source 213 and the MRI magnet assembly 214 are coupled to the rotating gantry 222 which is supported by a frame such that the radiation source 213 and the magnet assembly 214 can be rotated in unison to image and treat the patient.

In this particular embodiment, the radiation source 213 comprises a collimating device 224 that is configured to shape the treatment beam radiating from the radiation source 213 to treatment the patient on the treatment couch 216. The axis defined by the treatment beam generated by the radiation source 213 is generally parallel to the axis defined by the poles 218 and 220 of the magnet assembly 214.

In this particular embodiment, the biplanar MRI magnet assembly 214 comprises a biplanar magnet having a pair of opposing biplanar magnet poles 218 and 220, and a biplanar gradient coil set 223. At least pole 218, the pole closest to the radiation source 213, includes a centrally located open bore sized to allow the treatment beam generated by the radiation source 213 to pass through and treat a patient on the patient treatment couch 216. While the poles 218 and 220 are shown in FIG. 10 as being above and below the patient, as the gantry 222 rotates around the patient treatment couch 216 the biplanar MRI magnet 214, the poles 218 and 220 may move 360 degrees around the treatment couch 216. The gradient coil set 223 of the magnet assembly 214 is configured to generate a divergent magnetic gradient field shaped to match the divergent geometry of the treatment beam of the radiation source 213. The treatment beam generated by the radiotherapy radiation source 213 is configured to pass through the open bore of the pole 218 of the MRI magnet assembly 214 during operation.

Figure 11:
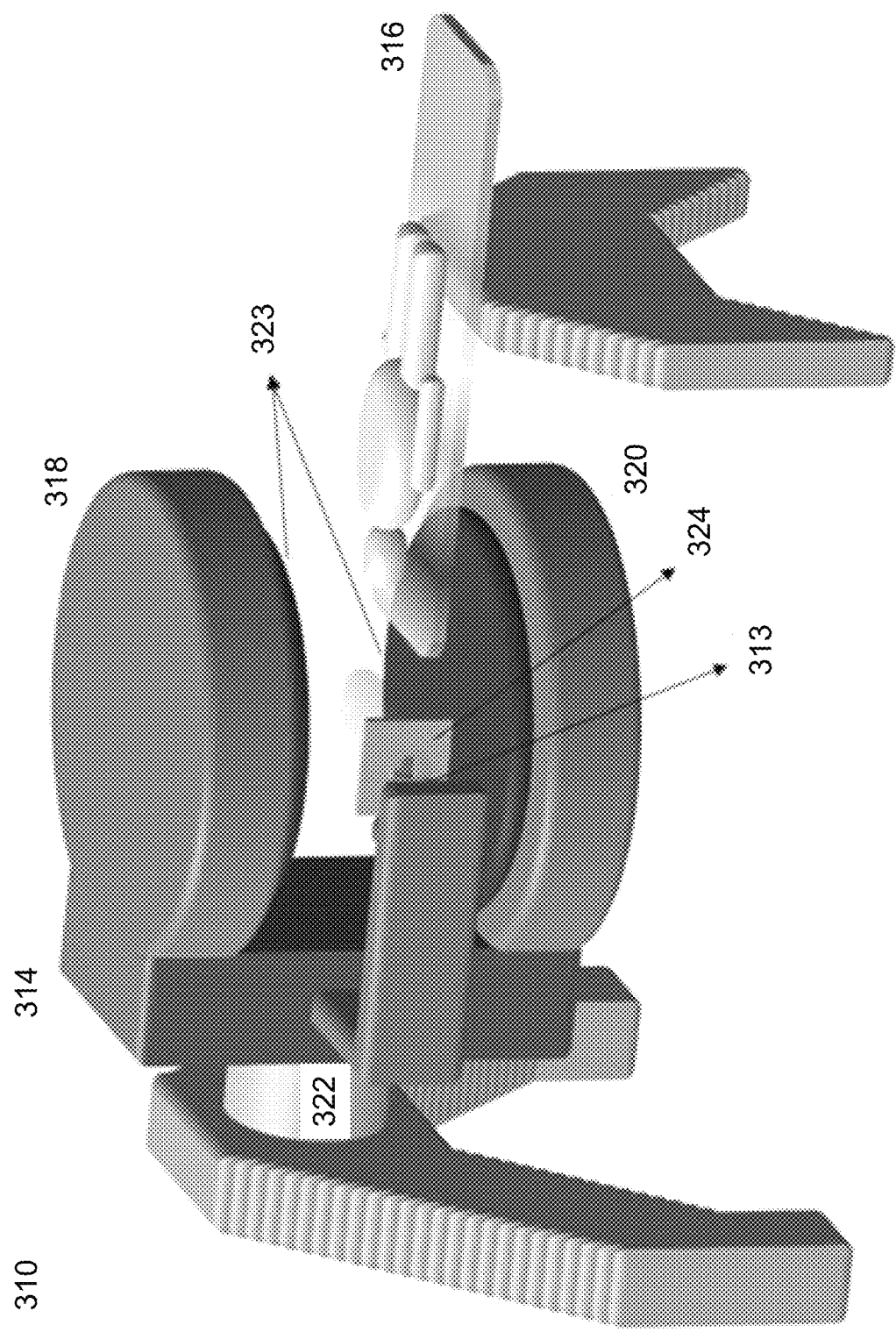
FIG. 11 is an isometric view of another embodiment of an integrated radiation source accelerator and magnetic resonance imaging (MRI) system.

Turning now to FIG. 11, another embodiment of an integrated radiation source and MRI system is shown and is generally identified by reference numeral 310. As can be seen, the integrated radiation source and MRI system 310 comprises a radiotherapy radiation source 313, a biplanar MRI magnet assembly 314, a patient treatment couch 316 and a rotating gantry 322. The radiotherapy radiation source 313 is configured to generate a treatment beam. The MRI magnet assembly 314 is configured to image a patient positioned on the patient treatment couch 316 in real time. The radiotherapy radiation source 313 and the MRI magnet assembly 314 are coupled to the rotating gantry 322 which is supported by a frame such that the radiation source 313 and the magnet assembly 314 can be rotated in unison to image and treat the patient.

In this particular embodiment, the radiation source 313 comprises a collimating device 324 that is configured to shape the treatment beam radiating from the radiation source 313 to treatment the patient on the treatment couch 316. The axis defined by the treatment beam generated by the radiation source 313 is generally perpendicular to the axis defined by the poles 318 and 320 of the magnet assembly 314.

In this particular embodiment, the biplanar MRI magnet assembly 314 comprises a biplanar magnet having a pair of opposing biplanar magnet poles 318 and 320, and a biplanar gradient coil set 323. While the poles 318 and 320 are shown in FIG. 11 as being above and below the patient, as the gantry 322 rotates around the patient treatment couch 316 the biplanar MRI magnet 314, the poles 318 and 320 may move in 360 degrees around the treatment couch 316. The gradient coil set 323 of the magnet assembly 314 is configured to generate a divergent magnetic gradient field shaped to match the divergent geometry of the treatment beam of the radiation source 313.

Figure 12:
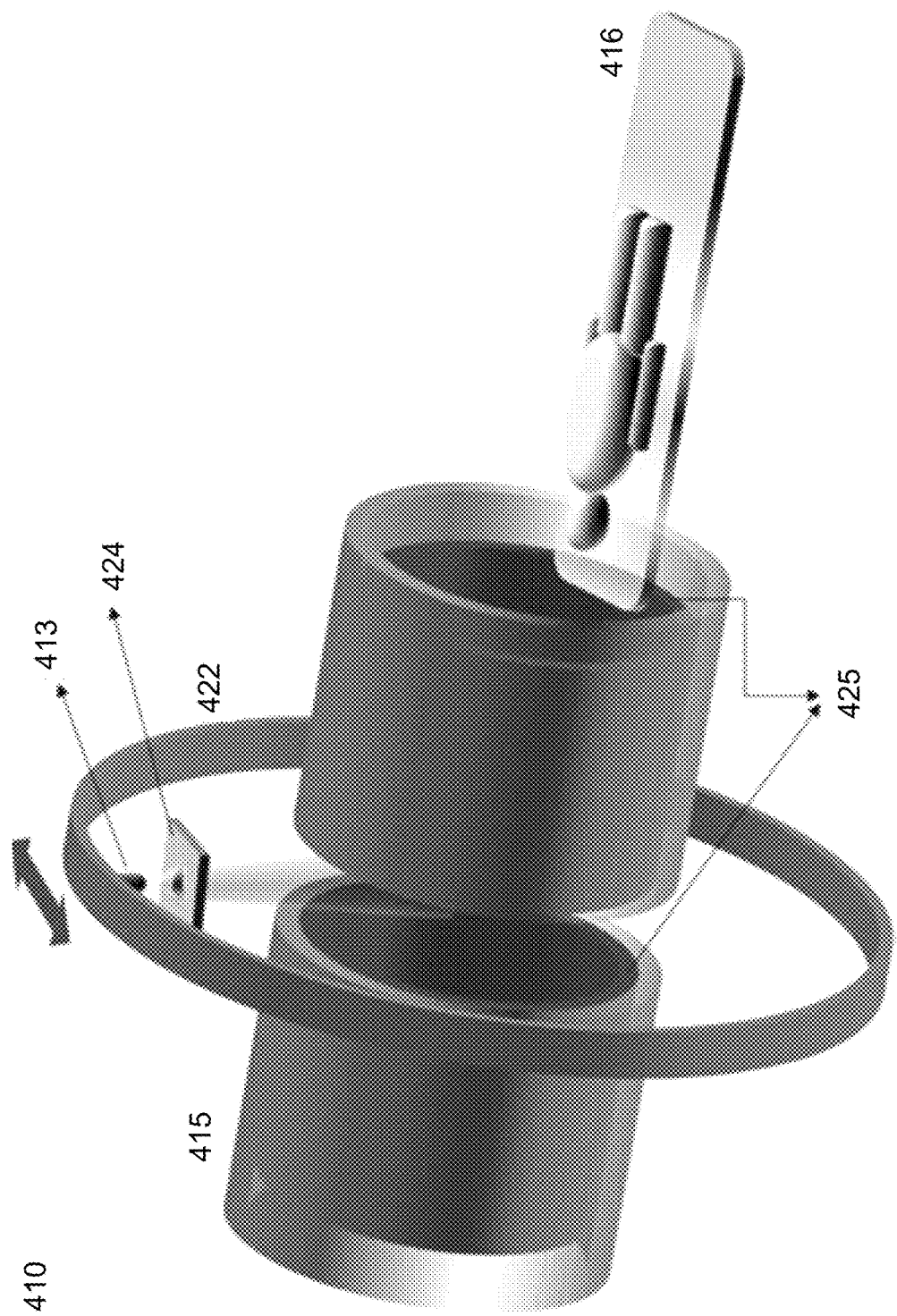
FIG. 12 is an isometric view of another embodiment of an integrated radiation source accelerator and magnetic resonance imaging (MRI) system.

Turning now to FIG. 12, another embodiment of an integrated radiation source and MRI system is shown and is generally identified by reference numeral 410. As can be seen, the integrated radiation source and MRI system 410 comprises a radiotherapy radiation source 413, a cylindrical MRI magnet assembly 415, a patient treatment couch 416 and a rotating gantry 422. The radiotherapy radiation source 413 is configured to generate a treatment beam. The MRI magnet assembly 415 is configured to image a patient positioned on the patient treatment couch 416 in real time.

In this particular embodiment, the radiation source 413 comprises a collimating device 424 that is configured to shape the treatment beam radiating from the radiation source 413 to treatment the patient on the treatment couch 416. The treatment beam generated by the radiation source 413 passes between elements of the cylindrical magnet assembly 416 as shown in FIG. 12. The radiation source 413 is coupled to the gantry 422 such that the radiation source 413 can treat any party of the patient on the patient treatment couch 416 through rotation of the gantry 422. In this particular embodiment, the radiation source 413 comprises a collimating device 424 that is configured to shape the treatment beam radiating from the radiation source 413 to treatment the patient on the treatment couch 416.

In this particular embodiment, the cylindrical MRI magnet assembly 414 comprises a pair of cylindrical magnets and a cylindrical gradient coil set 425. The gradient coil set 425 comprises two gradient magnets which are within the cylindrical magnets. The axis defined by the treatment beam generated by the radiation source 413 is generally perpendicular to the axis defined by the cylindrical magnets of the cylindrical MRI magnet assembly 414. The gradient coil set 425 of the magnet assembly 414 is configured to generate a divergent magnetic gradient field shaped to match the divergent geometry of the treatment beam of the radiation source 413.

Although embodiments of the invention have been described herein, it will be understood by those skilled in the art that variations may be made thereto without departing from the scope of the appended claims.

What is claimed is:

1. A magnetic resonance-radiotherapy system for treating a patient, the magnetic resonance-radiotherapy system comprising:
   a radiation source configured to supply a radiation beam to treat the patient, the radiation beam diverging as it travels from the radiation source; and a magnetic resonance imaging apparatus configured to generate a divergent gradient field shaped to match a divergent geometry of the radiation beam of the radiation source.

2. The magnetic resonance-radiotherapy system of claim 1, wherein the magnetic resonance imaging apparatus comprises at least one gradient coil configured to generate the divergent gradient field shaped to match the divergent geometry of the radiation beam of the radiation source.

3. The magnetic resonance-radiotherapy system of claim 2, wherein the magnetic resonance imaging apparatus comprises two gradient coils configured to generate the divergent gradient field shaped to match the divergent geometry of the radiation beam of the radiation source.

4. The magnetic resonance-radiotherapy system of claim 2, wherein the at least one gradient coil comprises windings of conductive material.

5. The magnetic resonance-radiotherapy system of claim 1, wherein the magnetic resonance imaging apparatus is configured such that image pixels are summed over a same divergent path as the radiation beam.

6. The magnetic resonance-radiotherapy system of claim 5, wherein the image pixels are summed in a direction in-line with the divergent path of the radiation beam.

7. The magnetic resonance-radiotherapy system of claim 1, wherein the magnetic resonance imaging apparatus comprises at least one gradient coil configured to generate an in-plane encoding gradient field for an image slice oriented perpendicular to a source-to-isocenter axis.

8. The magnetic resonance-radiotherapy system of claim 7, wherein the magnetic resonance imaging apparatus comprises at least one other gradient coil configured to generate the divergent gradient field shaped to match the divergent geometry of the radiation beam of the radiation source.

9. The magnetic resonance-radiotherapy system of claim 8, wherein the at least one gradient coil and the at least one other gradient coil in combination generate the divergent gradient field.

10. The magnetic resonance-radiotherapy system of claim 8, wherein the at least one other gradient coil generates the divergent gradient field independently of the at least one gradient coil.

11. The magnetic resonance-radiotherapy system of claim 7, further comprising a control system configured to toggle the at least one gradient coil and the at least one other gradient coil to switch between the transverse gradient field and the divergent gradient field.

12. The magnetic resonance-radiotherapy system of claim 1, wherein the radiation source and the magnetic resonance imaging apparatus are mounted to a common rotating gantry.

13. The magnetic resonance-radiotherapy system of claim 1, wherein rotation of the radiation source is independent of the gradient coils.

14. The magnetic resonance-radiotherapy system of claim 13, wherein the magnetic resonance imaging apparatus comprises gradient coils configured to generate the divergent gradient field shaped to match the divergent geometry of the radiation beam of the radiation source at one or a plurality of beam positions.

15. The magnetic resonance-radiotherapy system of claim 14, wherein the gradient coils are $2^{nd}$ order field gradients.

16. The magnetic resonance-radiotherapy system of claim 1, wherein an encoding gradient of the magnetic resonance imaging apparatus is configured to generate a field that approximates:

$$G_i(x, y, z) \propto \frac{SID}{SID + \hat{r}_s \cdot \langle x, y, z \rangle} \hat{r}_i \cdot \langle x, y, z \rangle,$$

wherein $\hat{r}_i$ represents a unit vector identifying a direction of an encoding axis perpendicular to a source-to-isocenter axis, wherein $\hat{r}_s$ represents a unit vector identifying a direction of the source-to-isocenter axis, and wherein SID represents a distance between the radiation source and a magnetic isocenter of the magnetic resonance imaging apparatus.

* * * * *